(12) United States Patent
Akifumi

(10) Patent No.: US 9,216,009 B2
(45) Date of Patent: Dec. 22, 2015

(54) CATHETER

(75) Inventor: Ishiguro Akifumi, Nagakute (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 949 days.

(21) Appl. No.: 13/409,555

(22) Filed: Mar. 1, 2012

(65) Prior Publication Data

US 2012/0165680 A1 Jun. 28, 2012

Related U.S. Application Data

(63) Continuation of application No. PCT/JP2010/065019, filed on Sep. 2, 2010.

(30) Foreign Application Priority Data

Sep. 4, 2009 (JP) .................................. 2009-205143

(51) Int. Cl.
*A61B 8/12* (2006.01)
*A61B 8/00* (2006.01)
*A61B 8/08* (2006.01)
*A61M 25/01* (2006.01)
*A61M 25/06* (2006.01)
*A61M 25/00* (2006.01)

(52) U.S. Cl.
CPC ... *A61B 8/12* (2013.01); *A61B 8/42* (2013.01); *A61B 8/445* (2013.01); *A61B 8/4461* (2013.01); *A61B 8/0891* (2013.01); *A61M 25/0113* (2013.01); *A61M 25/0662* (2013.01); *A61M 2025/0004* (2013.01)

(58) Field of Classification Search
CPC ...................... A61M 25/0108; A61M 25/0105; A61M 25/0158; A61M 25/0113; A61M 2019/5278; A61M 2019/528; A61M 2019/5282; A61M 2019/5285; A61M 2025/0002; A61M 2025/0004; A61M 2025/0166; A61M 1/0025; A61M 2019/5263
See application file for complete search history.

(56) References Cited

U.S. PATENT DOCUMENTS

2010/0010476 A1 * 1/2010 Galdonik et al. ............. 604/529

FOREIGN PATENT DOCUMENTS

| JP | 10-234735 A | 9/1998 |
|---|---|---|
| JP | 2002-360578 A | 12/2002 |
| JP | 2005-013453 A | 1/2005 |
| JP | 2006-075530 A | 3/2006 |
| JP | 2006075530 A * | 3/2006 |

OTHER PUBLICATIONS

International Search Report (PCT/ISA/210) issued on Oct. 12, 2010, by Japanese Patent Office as the International Searching Authority for International Application No. PCT/JP2010/065019.

* cited by examiner

*Primary Examiner* — Nicholas Lucchesi
*Assistant Examiner* — Anh Bui
(74) *Attorney, Agent, or Firm* — Buchanan Ingersoll & Rooney PC

(57) ABSTRACT

A catheter includes a sheath insertable inside a body lumen and provided with a window portion permeable to inspection waves, a detection unit movable in the axial direction of the sheath inside the sheath and which detects the inspection waves, and a reinforcement tube positionable to cover the inner surface or the outer surface of the window portion and movable in the axial direction of the sheath.

20 Claims, 15 Drawing Sheets

FIG. 12
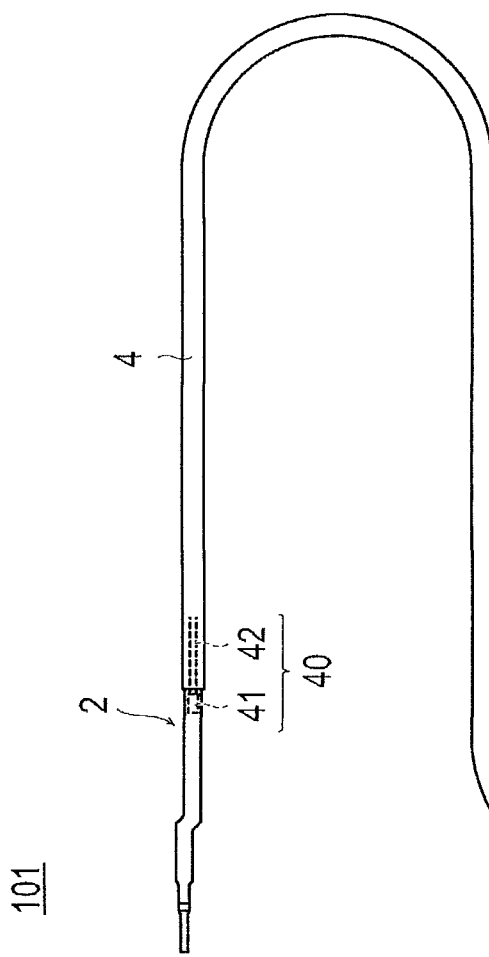
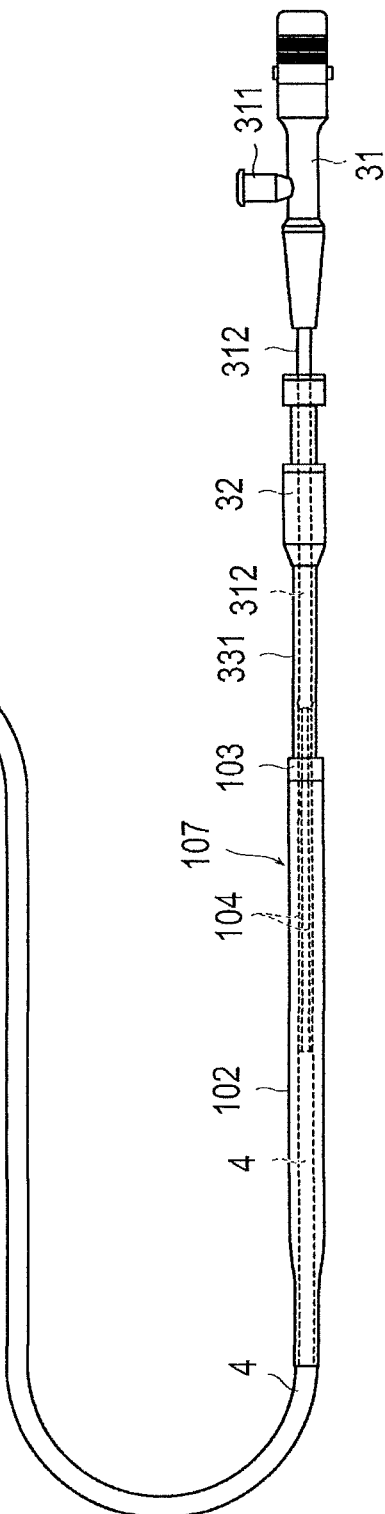

CATHETER

This application is a continuation of International Application No. PCT/JP2010/065019 filed on Sep. 2, 2010, and claims priority to Japanese Application No. 2009-205143 filed on Sep. 4, 2009, the entire content of both of which is incorporated herein by reference.

TECHNICAL FIELD

The present invention generally relates to a catheter. More specifically, the invention involves a catheter having useful application for being inserted inside a body lumen such as a blood vessel, a vascular channel and the like.

BACKGROUND DISCUSSION

To examine a target lesion inside a body lumen such as a blood vessel, a vascular channel and the like, an ultra-sound catheter is used to transmit and receive an ultra-sound at the target lesion. For example, the ultra-sound catheter described in Japanese Unexamined Patent publication No. 2002-360578 includes a transducer unit for transmitting and receiving an ultra-sound, an imaging core provided with a drive shaft for rotating this transducer unit and a sheath for covering this imaging core and concurrently for being inserted inside the body lumen. The imaging core is movable in an axial direction inside the sheath. The sheath is formed with an acoustic window portion through which an ultra-sound from the transducer unit is penetratable.

When using the ultra-sound catheter, the imaging core is first arranged beforehand on the most distal side inside the sheath and concurrently the sheath is carried to a position beyond the target lesion, and next, while leaving the sheath alone, only the imaging core is continued to back away from the sheath distal end along the acoustic window portion and passed through the target lesion. By making only the imaging core back away, the transducer unit moves by passing through the target lesion from the deep portion, so that it is possible to observe the ultra-sound continuously over a region before and after the target lesion and also to produce a tomographic image of a shape such as a blood vessel, a vascular channel and the like. It is also possible to carry out reconfirmation of the target lesion and a production of the tomographic image by advancing the imaging core which was once backed away.

However, it is not possible for the acoustic window portion through which the ultra-sound passes to contain a structural body which can reflect the ultra-sound. As a result, depending on the material used for the acoustic window portion, there is sometimes a case in which rigidity is low, pressureability, anti-kink property, following-ability or the like is low, and work performance is low.

SUMMARY

The disclosure here involves a catheter comprising: a sheath configured to be positioned in a body lumen of a living body and including a window portion permeable to inspection waves; a detection unit which receives inspection waves reflected from tissue of the body lumen and passing through the window portion of the sheath, with the detection unit axially movably positioned inside the sheath; a drive shaft connected to the detection unit so that axial movement of the drive shaft results in axial movement of the detection unit, wherein the drive shaft is positioned inside the sheath; a reinforcement tube positionable to axially overlap the window portion of the sheath and reinforce a portion of the sheath that includes the window portion, with the reinforcement tube being axially movable relative to the sheath to vary an amount of axial overlap of the reinforcement tube and the window portion of the sheath; and a hub connected to the drive shaft so that axial movement of the hub results in axial movement of the drive shaft and the detection unit, and wherein the reinforcement tube possesses a proximal-most end located distally of the proximal-most end of the hub.

According to another aspect, a catheter includes: a sheath configured to be positioned in a body lumen of a living body and provided with a window portion permeable to inspection waves; a detection unit which detects the inspection waves passing through the window portion of the sheath, wherein the detection unit is positioned inside the sheath and is axially movable inside the sheath; and a reinforcement tube axially movable relative to the sheath so that the reinforcement tube is positionable to cover the inner surface or the outer surface of the window portion of the sheath.

It is possible for the catheter to be configured so that the inner surface or the outer surface of the window portion is covered by the reinforcement tube which is movable in the axial direction of the sheath, so that during use of the catheter, it is possible to cover the window portion with the reinforcement tube or to expose the window portion. Consequently, for example, when inserting the sheath inside the body lumen, it is possible, by covering the window portion with the reinforcement tube, to improve pressureability, anti-kink property and steerability such as following-ability, and it is possible to move it to the aimed or desired position. Also, when carrying out observation by a detection unit, it is possible, by moving the reinforcement tube and by exposing the window portion, to carry out the observation through the window portion having high permeability for the inspection wave. The catheter can include a reinforcement tube steering unit for moving the reinforcement tube in the axial direction of the sheath, thus making it possible to move the reinforcement tube relatively freely by the reinforcement tube steering unit while also improving work performance.

The reinforcement tube steering unit can include a case main body attached to the sheath and a manually rotatable rotation member rotatably mounted in the main body to move the reinforcement tube by a rotation force. By rotating the rotation member manually, it is possible to move the reinforcement tube and improve work performance.

The catheter can also be constructed such that the reinforcement tube and the detection unit are axially fixed relative to one another so that the reinforcement tube is not axially movable relative to the detection unit, and wherein the distal-most end of the reinforcement tube is positioned proximally of the distal end of the detection unit so that the distal-most end of the detection unit is distal of the distal-most end of the reinforcement tube. It is thus possible, while exposing the window portion in the region at which the detection unit is positioned always in an observable state, to reinforce the window portion on the sheath proximal side away from the detection unit by the reinforcement tube. Also, the reinforcement tube and the detection unit are moved simultaneously, so that it is not necessary to steer the reinforcement tube and the detection unit separately and the work performance thereof is excellent.

The catheter can also include a drive shaft positioned inside the sheath and fixed to the detection unit to transmit a mechanical driving force to the detection unit by way of the drive shaft, and a hub for axially moving the drive shaft in an axial direction of the sheath, and wherein the reinforcement tube is interlinked to the hub and is axially movable together with the hub and the drive shaft. It is thus possible, by moving the hub, to move the detection unit and the reinforcement tube simultaneously so that the work performance of the catheter is quite good.

The sheath can include a housing unit configured to accommodate the detection unit on the sheath distal side away from the window portion. Housing the detection unit in the housing unit, it is possible to cover the window portion completely with the reinforcement tube positioned on the sheath proximal side away from the detection unit and the whole window portion can be reinforced.

Another aspect involves a method comprising: inserting a catheter in a body lumen of a living body, wherein the catheter comprises a sheath provided with a window portion permeable to inspection waves, a detection unit axially movably positioned inside the sheath, and a reinforcement tube axially movable relative to the sheath and axially covering the window portion of the sheath; moving the catheter until a distal end portion of the catheter is positioned adjacent a target lesion in the body lumen; axially moving the reinforcement tube in a proximal direction to uncover the window portion of the sheath; directing inspection waves at the body lumen; and receiving at the detection unit reflected inspection waves which have reflected off the body lumen and passed through the window portion of the sheath.

BRIEF DESCRIPTION OF DRAWINGS

FIG. 12 is a plan view of an ultra-sound catheter according to a third embodiment disclosed by way of example.

DETAILED DESCRIPTION

A first embodiment of an ultra-sound catheter 1 (catheter) disclosed here by way of example includes a sheath 2 configured (e.g., sized) to be inserted inside a body lumen, a reinforcement tube 4 which reinforces the sheath 2 and a steering unit 3 which is not inserted inside the body lumen and arranged on the side of the user to be steered by the user.

Figure 2:
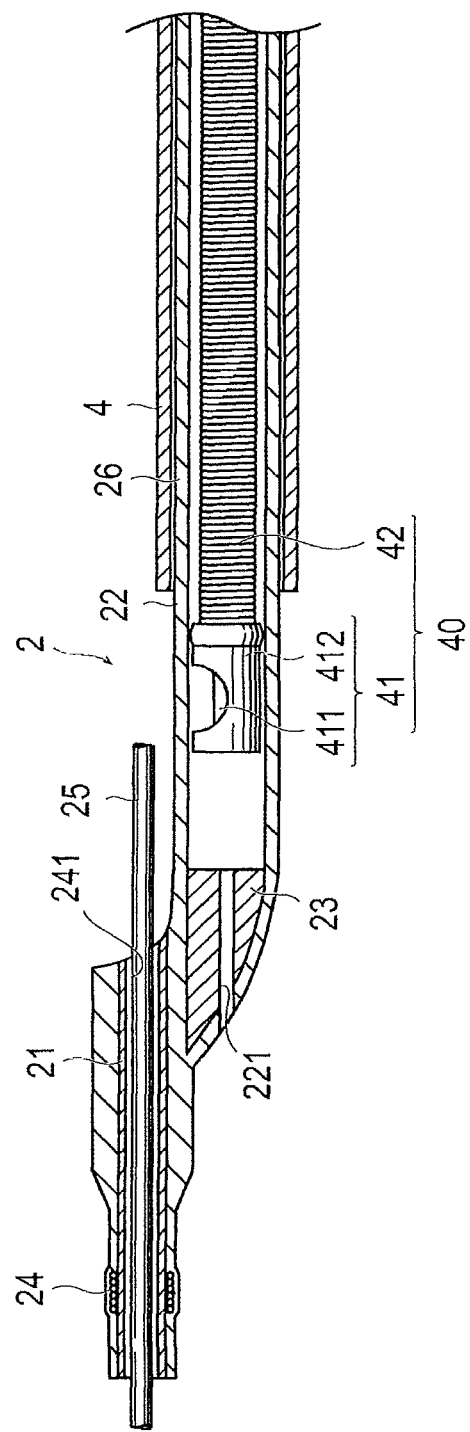
FIG. 2 is a longitudinal cross-sectional view of a junction portion between a distal portion and a main body unit of the ultra-sound catheter.

The sheath 2 includes, as shown in FIG. 2, a sheath distal member 21, a sheath main body unit 22 and a filling-liquid in/out-path member 23. The sheath main body unit 22 is bonded with or fixed to the sheath distal member 21 and the filling-liquid in/out-path member 23 so as to cover the sheath distal member 21 and the filling-liquid in/out-path member 23.

An X-ray imaging marker 24 is provided between the outer surface of the sheath distal member 21 and the inner surface of the sheath main body unit 22. The X-ray imaging marker 24 is configured such that the distal position of the ultra-sound catheter can be confirmed under X-ray fluoroscopy when positioned inside the body lumen.

The sheath distal member 21 is formed with a hole 241 and a guide wire 25 is inserted and passed through this hole 241. The guide wire 25 is inserted inside the body lumen beforehand and the ultra-sound catheter 1 is then introduced to the target lesion while passing this guide wire 25 through the sheath distal member 21 (i.e., while the catheter 1 is guided along the guide wire 25 toward the target lesion).

Also, the filling-liquid in/out-path member 23 and the sheath main body 22 are formed with a priming lumen 221 which is a hole for allowing a physiological saline solution filled inside the sheath main body unit 22 to flow to the outside.

The imaging core 40 is slidably installed in the sheath 2 in an axial direction of the sheath 2. This imaging core 40 includes a transducer unit 41 (detection unit) for transmitting the ultra-sound (inspection wave) toward a tissue inside the body lumen and for receiving a reflected ultrasound wave a drive shaft 42 which is attached or fixed to this transducer unit 41 at a distal end of the drive shaft 42 and concurrently rotates the transducer unit. The transducer unit 41 includes an ultrasonic transducer 411 for transmitting and receiving the ultrasound and an ultrasonic transducer housing 412 for housing the ultrasonic transducer 411.

Figure 4:
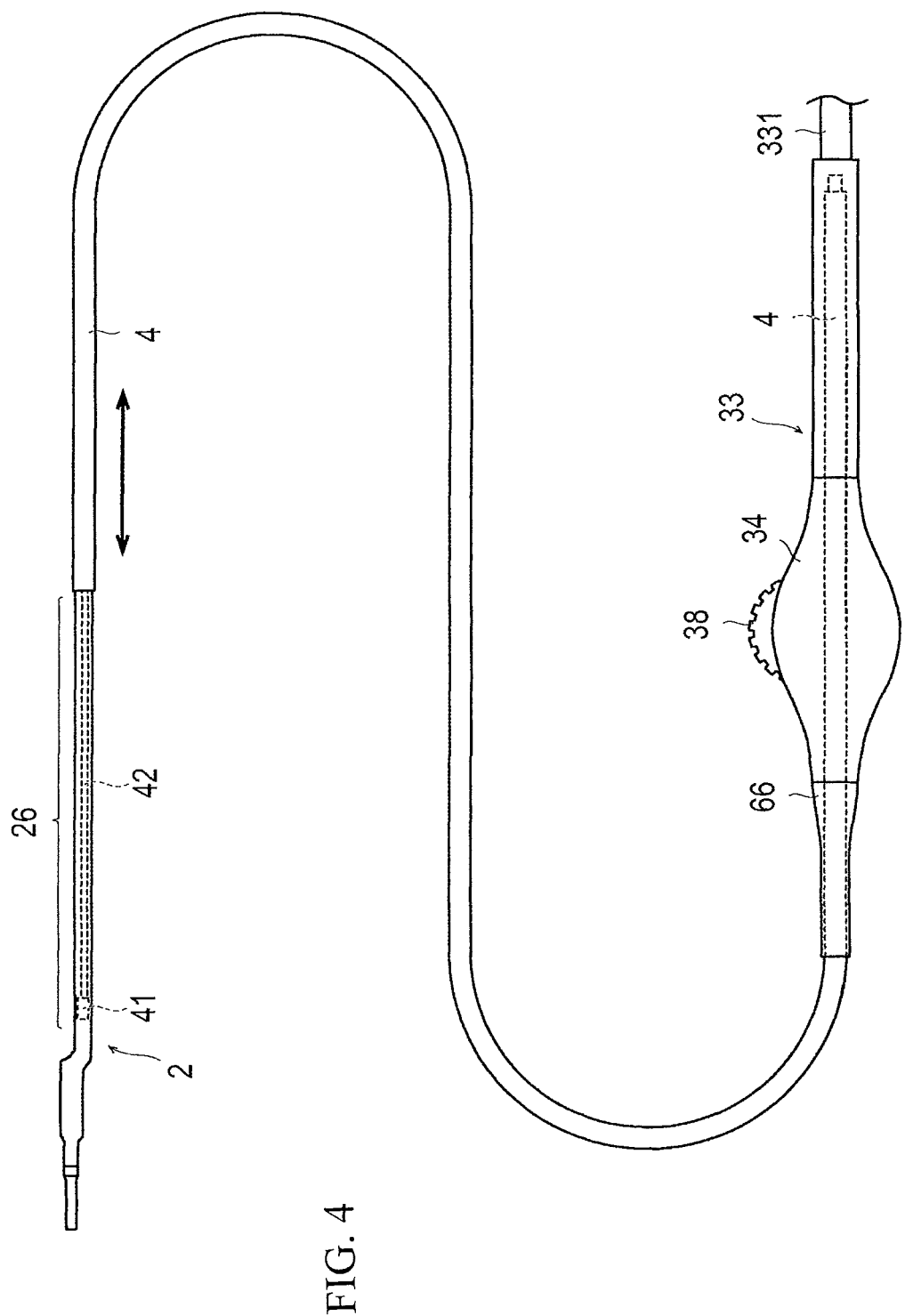
FIG. 4 is a plan view of the ultra-sound catheter when moving a reinforcement tube toward the proximal side maximally.

The sheath 2 is formed by a material which exhibits relatively high ultra-sound permeability. Referring to FIG. 4, a site within an area in which the ultrasonic transducer 411 of the sheath 2 moves constitutes an acoustic window portion 26 (window portion). Ultra-sound has a reflection property at which the ultra-sound is reflected at a boundary portion at which acoustic impedance changes. During diagnosis, more specifically, in a state in which the ultra-sound catheter 1 is indwelled in a blood vessel, the surrounding area of the ultrasound catheter 1 is filled with blood (body liquid). Therefore, it is necessary that a substance having an equivalent acoustic impedance other than that of the blood does not exist between the ultrasonic transducer 411 and a blood vessel wall which is a diagnosis target. It should be noted that the acoustic impedance is a constant peculiar to a material, which is expressed by a product of acoustic speed in the material (speed of sound) and density of the material. In an intraluminal side of the sheath 2, there is injected, as an ultra-sound transmission liquid, a physiological salt solution (saline solution) whose acoustic impedance approximately coincides with that of blood. Therefore, it is also necessary for the material constituting the sheath 2 to be a material having an equivalent acoustic impedance. One example of the material for the sheath 2 is polyethylene.

The reinforcement tube 4 is a tubular member covering the outside or outer surface of the sheath 2. With respect to the illustrations in FIG. 3 and FIG. 4, the reinforcement tube 4 is movable in the axial direction with respect to the sheath 2. The reinforcement tube 4 is a reinforcing member which reinforces the sheath 2 having low rigidity and it is preferably formed of a high strength metal or resin. There is no limitation for the material or for the construction of the reinforcement tube 4 so long as the reinforcement purpose is achieved. In this embodiment disclosed by way of example, the reinforcement tube 4 is a tubular body made of stainless steel, which is applied with a cut process in a spiral shape. That is, the tube 4 is provided with a spiral-shaped slit.

When the reinforcement tube 4 is moved toward the distal side or in the distal direction to a maximum extent, the reinforcement tube 4 covers the whole of the acoustic window portion 26 (see FIG. 3), and when the reinforcement tube 4 is pulled-in toward the proximal side or in the proximal direction to a maximum extent, the acoustic window portion 26 is completely exposed by positioning the distal side of the reinforcement tube 4 on the proximal side of the acoustic window portion 26 of the sheath 2 (see FIG. 4).

The drive shaft 42 shown in FIG. 2 is flexible, yet is also configured so that a rotational motion power produced in the steering unit 3 is transmitted to the transducer unit 41. By way of example, the drive shaft 42 can be constituted by a tube body of a multi-layer coil shape such as a three-layer coil whose winding direction alternates in a manner from right to left and again right. Owing to a fact that the drive shaft 42 is configured to transmit rotational motion power, the transducer unit 41 rotates and it is possible to observe 360 degrees of the target lesion inside the body lumen of such as a blood vessel, a vascular channel and the like. Also, a signal line passes through the inside of the drive shaft 42 to transmit a signal detected by the transducer unit 41 to the steering unit 3 (see FIG. 1).

Figure 1:
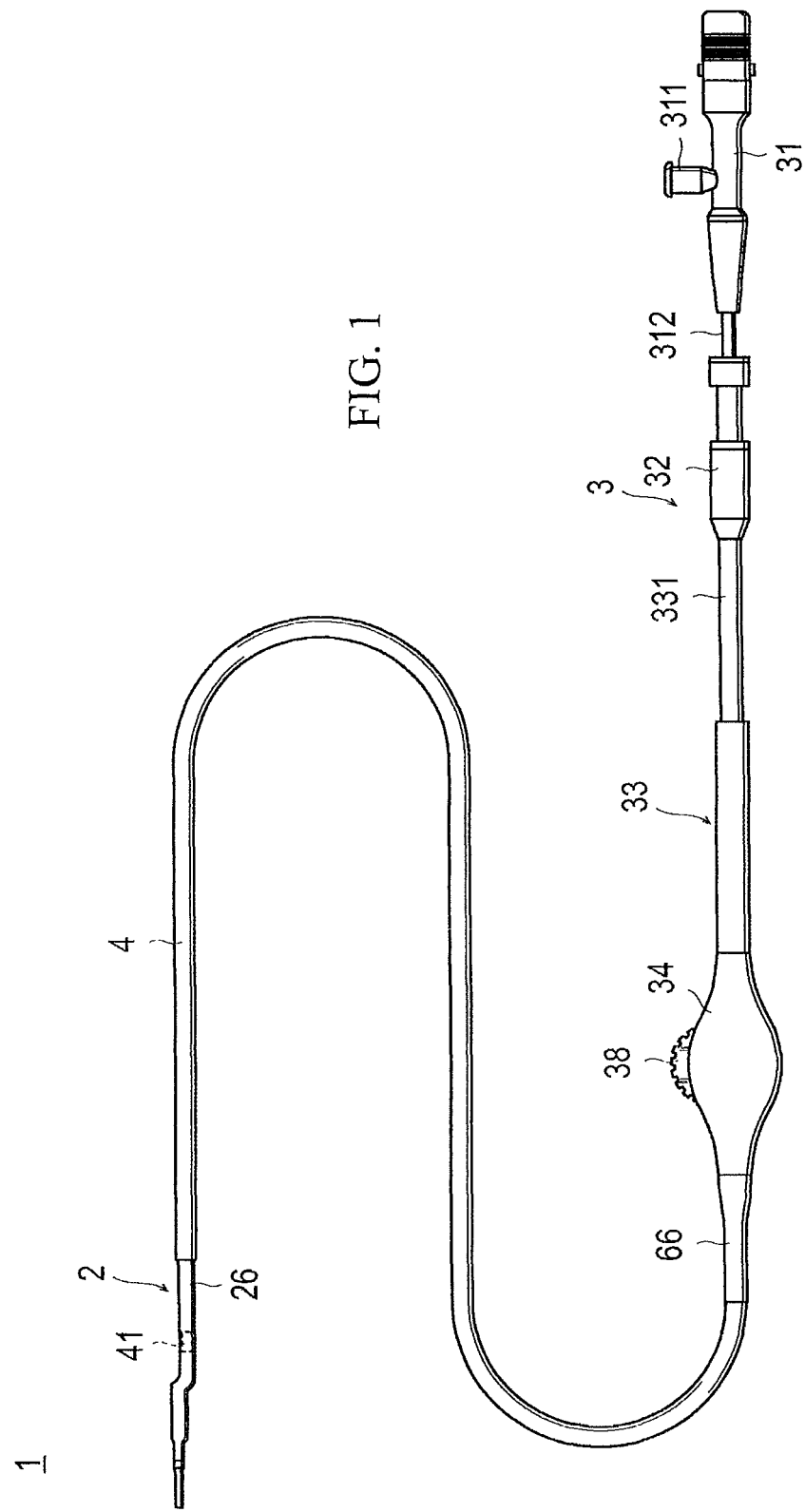
FIG. 1 is a plan view of one example of an ultra-sound catheter disclosed here.

The steering unit 3 includes, as shown in FIG. 1, a hub 31 having a port 311 for injecting physiological salt solution for removing air, a unit connector 32 connected with the hub 31 through an inner tube 312 and a relay connector 33 which is connected to the unit connector 32 through the outer tube 331 and concurrently, which connects the sheath 2 and the steering unit 3. The relay connector 33 is provided with a reinforcement tube steering unit 34 for steering or controlling the movement (axial movement) of the reinforcement tube 4.

The hub 31 holds the drive shaft 42 and the inner tube 312. By pressing or moving the inner tube 312 into the unit connector 32 and the outer tube 331 or by pulling it out therefrom, the drive shaft 42 slides cooperatively inside steering unit 3 and the sheath 2 in the axial direction. An aspect of the movement of the drive shaft 42 involving the pressing and the pulling-out of the inner tube 312 is shown in FIG. 5 and FIG. 6.

Figure 5:
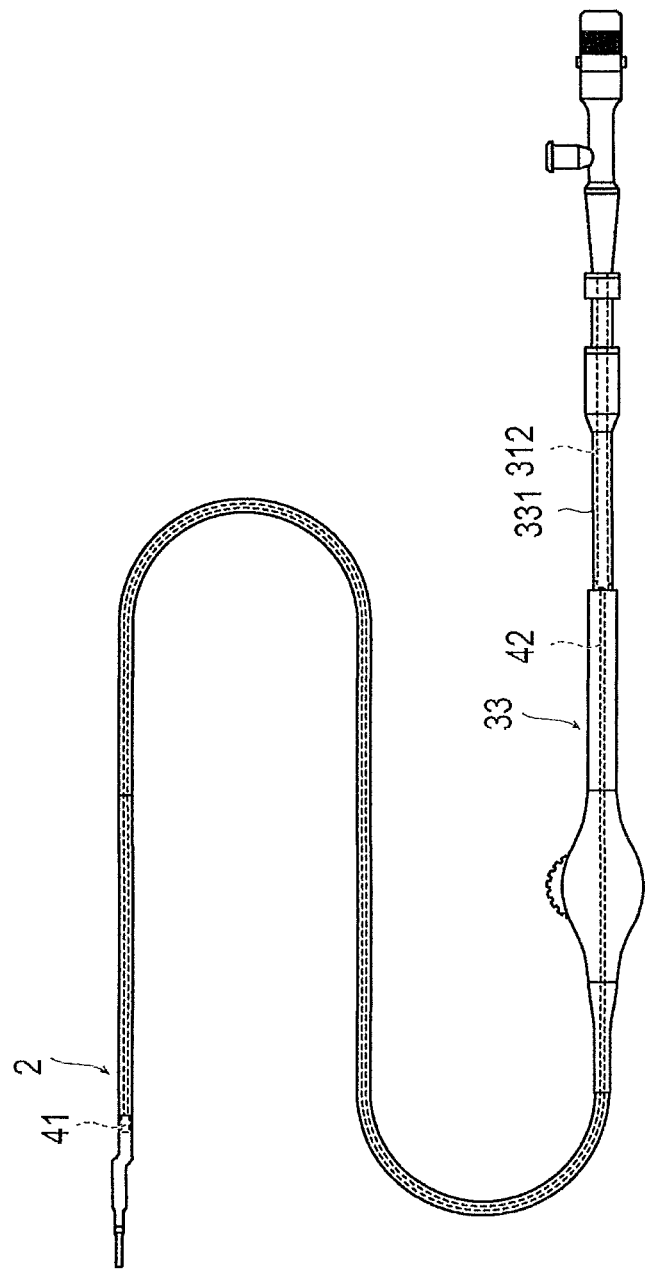
FIG. 5 is a plan view of the ultra-sound catheter when pressing an inner tube maximally with respect to a unit connector.

When the inner tube 312 is pushed-in or distally moved to a maximum extent, as shown in FIG. 5, with respect to the outer tube 331 an end portion of the inner tube 312 on the sheath side (i.e., the distal end of the inner tube 312) reaches the vicinity of the sheath side end portion (distal side end portion) of the outer tube 331, more specifically, the vicinity of the relay connector 33. Then, in this state, the transducer unit 41 is positioned in the vicinity of the distal end of the sheath main body unit 22 of the sheath 2.

Figure 6:
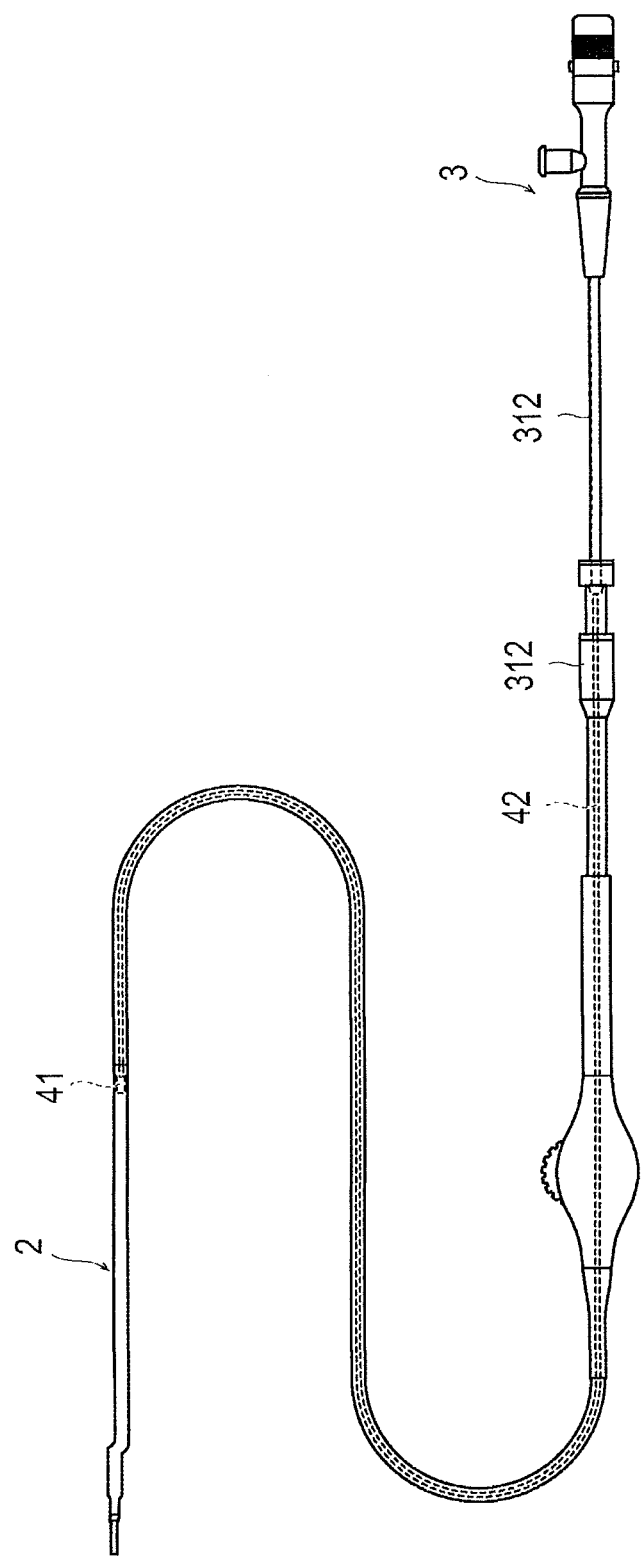
FIG. 6 is a plan view of the ultra-sound catheter when pulling out an inner tube maximally from a unit connector.
Figure 8:
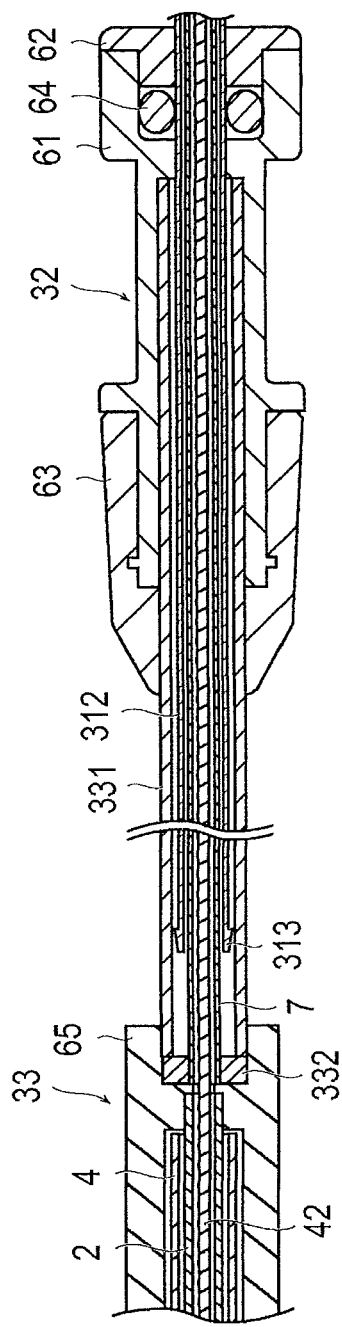
FIG. 8 is a longitudinal cross-sectional view of a unit connector and a relay connector.

Also, when the inner tube 312 is pulled-out or moved proximally to a maximum extent as shown in FIG. 6, a stopper 313 formed at the distal end of the inner tube 312 as shown in FIG. 8 engages the inner wall of the unit connector 32. At this point, other than the distal end portion of the inner tube 312 engaging the inner wall of the unit connector 32, the inner tube 312 is exposed. In this state, the transducer unit 41 is pulled back while remaining inside the sheath 2, so that it is positioned at a place toward the side of the steering unit 3 as much as pulling-out the inner tube 312. That is, the pull-back distance of the transducer unit 41 inside the sheath is equal to the pull-back distance of the inner tube 312. Owing to the fact that the transducer unit 41 moves while being rotated, it is possible to create a tomographic image of such as a blood vessel, a vascular channel and the like.

The following is a description of an example of a specific construction or configuration for each portion of the ultrasound catheter 1.

Figure 7:
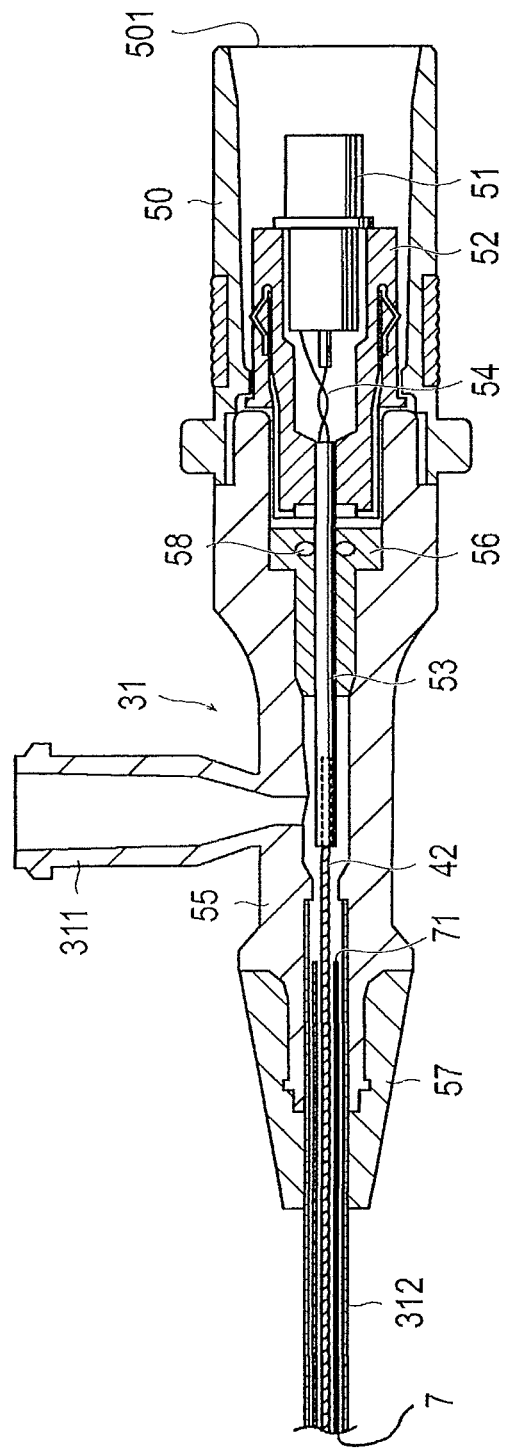
FIG. 7 is a longitudinal cross-sectional view of a hub.

As shown in FIG. 7, the hub 31 includes a joint 50, a male connector 51, a rotor 52, a connection pipe 53, a signal line 54, a hub main body 55, a seal member 56 and an anti-kink protector 57.

The joint 50 includes an opening portion or open end 501 on the hand-side of a user (proximal end) of the ultra-sound catheter 1. The male connector 51 and the rotor 52 are positioned in the joint 50. It is possible for the male connector 51 to connect with a female connector 711 included in an external drive apparatus 80 (see FIG. 10) from the opening portion 501 side of the joint 50 and thus, mechanical and electrical connection between the external drive apparatus 80 and the male connector 51 becomes possible.

Figure 10:
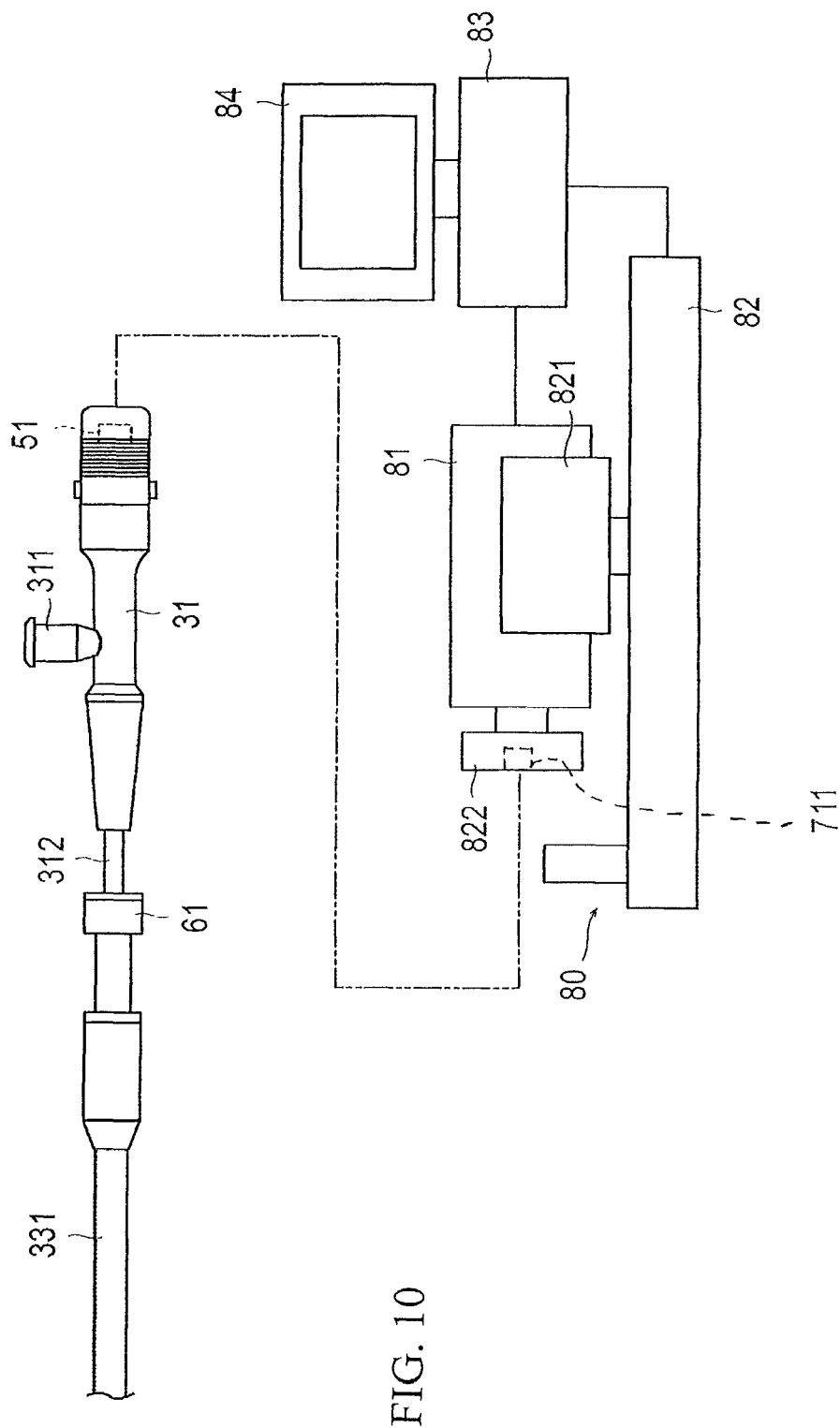
FIG. 10 is a schematic diagram showing a relationship between an ultra-sound catheter and an external drive apparatus.

The external drive apparatus 80 is, as shown in FIG. 10, composed of a scanner device 81 installed with an external drive power supply of a motor or the like, an axial direction moving device 82 which connects to the scanner device 81 and which causes or produces the axial direction movement depending on the motor and the like, a control unit 83 for controlling the scanner device 81 and the axial direction moving device 82 and a display unit 84 for displaying an image obtained by the transducer unit 41. The axial direction moving device 82 includes a scanner device grab portion 821 for connecting and fixing the scanner device 81 and a sheath support portion 822 which supports the sheath 2 so as not to be deviated at the time of the pulling-back thereof.

The scanner device 81 carries out transmission & reception of the signal from the transducer unit 41 by being connected to the male connector 51 and simultaneously transmits a driving force for rotating the drive shaft 42.

The ultra-sound scan in the ultra-sound catheter 1 is carried out by directing the ultra-sound which is transmitted and received by the ultrasonic transducer 411 provided in the housing 412 in approximately the radial direction by transmitting a rotational motion of the motor in the scanner device 81 to the drive shaft 42 and by rotating the housing 412 fixed at the distal end of the drive shaft 42. The ultra-sound image obtained here is a cross-sectional image inside the blood vessel. Also, by pulling the whole ultra-sound catheter 1 toward the hand-side (i.e., in the proximal direction) and by moving the imaging core 40 in the longitudinal direction, it is possible to obtain a 360° cross-sectional image at any desired position in a scanning manner in the surrounding tissues extending over the axial direction inside the blood vessel.

The rotor 52 holds, as shown in FIG. 7, the connection pipe 53 so that the connection pipe 53 does not rotate relative to the rotor 52. The end portion of the connection pipe 53 opposite the rotor 52 side holds or is fixed to the drive shaft 42 in order to transmit rotation of the rotor 52 to the drive shaft 42. The signal line 54 passes-through the inside of the connection pipe 53. One end of the signal line 54 is connected to the male connector 51, and the other end of the signal line 54 passes-through the inside of the drive shaft 42 and is connected to the transducer unit 41. Observation results in the transducer unit 41 are transmitted to the external drive apparatus 80 through the male connector 51, are appropriately processed, and are displayed as images.

The hub main body 55 is injected with the physiological salt solution from the port 311 and introduces this physiological salt solution into the inner tube 312 without leakage to the outside. It should be noted that there is installed with the seal member 56 including an O-ring 58 between the hub main body 55 and the joint 50, so that the physiological salt solution does not leak out to the opening portion 501 side of the joint 50.

With respect to the hub main body 55, a portion of the inner tube 312 is fit to the hub main body 55 by insertion, and the anti-kink protector 57 is arranged to surround a part of the inner tube 312 and the hub main body 55. The anti-kink protector 57 is formed of a material having an intermediate hardness between the hardness of the inner tube 312 and the hardness of the hub main body 55, and it is possible to prevent bending, twisting or the like of the inner tube 312 at the region in which the inner tube 312 is exposed from the hub main body 55.

A protection tube 7 is arranged inside the inner tube 312, between the drive shaft 42 and the inner tube 312. This protection tube 7 opens at the end portion on the hub 31 side and includes an end which is not held at all, that is, a free end 71. The protection tube 7 extends to the distal end of the outer tube 331 shown in FIG. 8.

The unit connector 32 includes, as shown in FIG. 8, a unit connector main body 61, a sealing member 62, a cover member 63 and a packing 64.

The outer tube 331 attached to the relay connector 33 is inserted into or positioned in the unit connector main body 61, and the inner tube 312 extending from the hub 31 is inserted inside or positioned in this outer tube 331. The sealing member 62 holds the packing 64 in combination with the unit connector main body 61, and the cover member 63 holds the outer tube 331 in combination with the unit connector main body 61. The packing 64 is sealed between the unit connector main body 61 and the sealing member 62, so that even if the physiological salt solution supplied to the port 311 of the hub 31 flows into the outer tube 331 through the inner tube 312, it does not leak to the outside of the unit connector 32.

Also, with respect to the inner tube 312 extending from the hub 31, a stopper 313 is formed at the distal end of the inner tube 312, so that when pulling the hub 31 to the maximum extent (moving the hub in the proximal direction to the maximum extent), more specifically even when pulling-out the inner tube 312 from the outer tube 331a maximum amount, the stopper 313 does not engage the inner wall of the unit connector main body 61 whereby the inner tube 312 will be pulled out from the unit connector 32.

Figure 9:
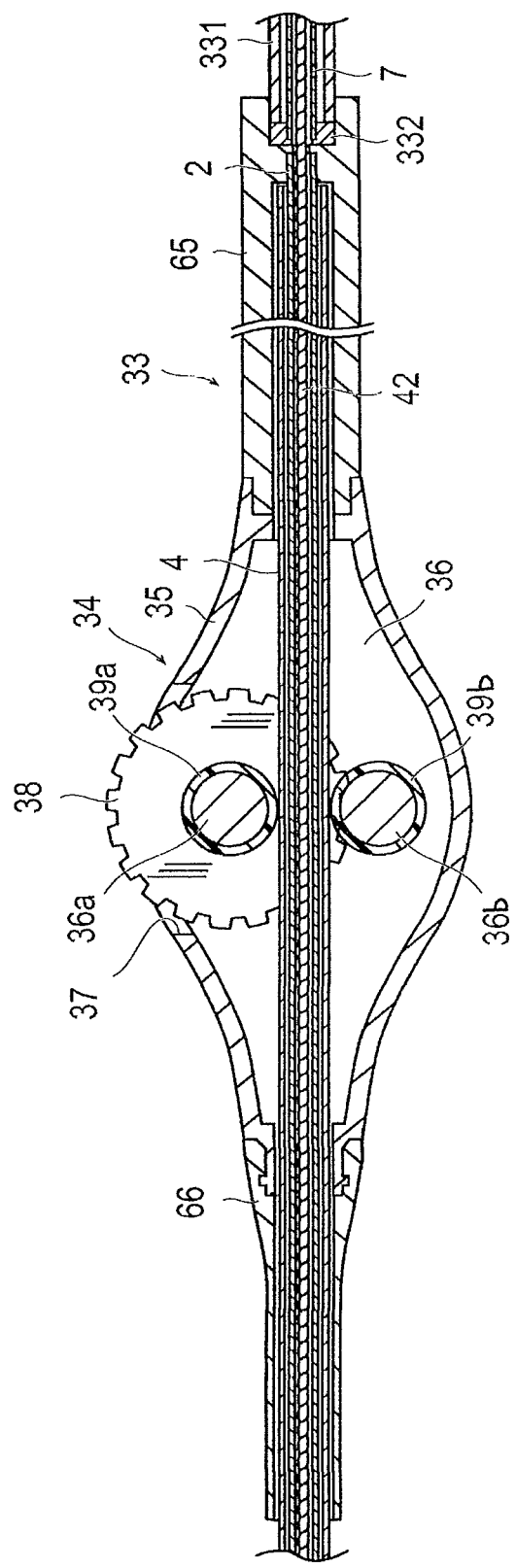
FIG. 9 is a longitudinal cross-sectional view of the relay connector.

The relay connector 33 includes, as shown in FIGS. 8 and 9, an outer tube hold portion 65, a relay connector main body 66 and a reinforcement tube steering unit 34. The outer tube hold portion 65 holds the outer tube 331. Also, the proximal side end portion of the sheath 2 is interlinked with or connected to the inner face of the outer tube hold portion 65, and a path exists for introducing the drive shaft 42 passing through from the outer tube 331 and the physiological salt solution into the sheath 2. It is also possible, by inserting a plurality of tubes further into the inside of this path, to inhibit or prevent buckling of the drive shaft 42, leakage of the physiological salt solution and the like.

The protection tube 7 is fixed on the inner wall of an exit member 332 (distal end wall of the outer tube 331) through which the drive shaft 42 of the outer tube hold portion 65 passes. This protection tube 7 extends toward the inside of the inner tube 312 extending from the hub 31. Consequently, when the inner tube 312 is pushed into the outer tube 331, the protection tube 7 is relatively moved inside the inner tube 312 in a direction opposite to the direction of pushing-in of the inner tube 312. When the inner tube 312 is pushed-in or pulled-out with respect to the outer tube 331 (i.e., when the inner tube 312 is moved distally or proximally relative to the outer tube 331), it happens that the protection tube 7 is also relatively pushed-in or pulled-out with respect to the inner tube 312 from the opposite direction, so that even if friction occurs by the contact with the inner tube 312 and a bending force occurs at the drive shaft 42, the bending force is repressed by the protection tube 7, and it is possible to prevent a bending or the like. It should be noted that the protection tube 7 is formed by a loosely wound coil shaped metal tube body and consequently, the physiological salt solution can flow into the coil by gaps in the coil and so air does not remain in the outer tube 331.

The reinforcement tube steering unit 34 includes a case main body 35 which is connected to the distal end portion of the outer tube hold portion 65. Inside the case main body 35 is formed a space portion 36 through which passes the sheath 2, the drive shaft 42 and the reinforcement tube 4. Two rotation members 36a, 36b are provided in the space portion 36. The two rotation members 36a, 36b are rotationally mounted in the case main body 35, and one of the rotation members 36a includes a coaxial operation dial 38. A portion of the outer circumferential surface of the operation dial 38 is exposed to the outside through an opening portion 37 in the case main body 35. The outer circumferential surface of the two rotation members 36a, 36b is each provided with a fixed high friction members 39a, 39b as slide stoppers which are composed of rubber or the like. The two rotation members 36a, 36b are arranged so that the reinforcement tube 4 is sandwiched between the high friction members 39a, 39b. Consequently, by manually rotating the operation dial 38 exposed to the outside, the rotation force of the rotation member 36a is transmitted to the reinforcement tube and it is possible to move the reinforcement tube 4 in the axial direction.

Also, it is possible to provide the reinforcement tube steering unit 34 with a lock mechanism for fixing the rotation member 36a (or 36b) against rotation at a desired rotational position. The lock mechanism can employ, for example, a construction or the like in which the lock mechanism is slidably provided on the case main body 35 such that it can approach and move away from the rotation member 36a or the rotation member 36b, whereby the approaching movement causes the lock mechanism to be engaged with the rotation member 36a or the rotation member 36b to fix the rotation members 36a, 36b against rotation.

The relay connector main body 66 is an anti-kink protector which is connected to the distal end portion of the reinforcement tube steering unit 34, and it helps prevents the bending (kink) of the reinforcement tube 4 and the sheath 2, which is caused by a rapid change of rigidity, while also covering and protecting the outer surface of the reinforcement tube 4.

As mentioned above, the ultra-sound catheter 1 disclosed here is configured to allow the inner tube 312 to be positioned in and axially moved in the outer tube 331. It is thus possible for a user to push and pull the hub 31 toward and away from the unit connector 32 to move the imaging core 40 inside the ultra-sound catheter 1 along the acoustic window portion 26. Then, by manually rotating the operation dial 38 of the reinforcement tube steering unit 34, the reinforcement tube 4 moves in the axial direction along the sheath 2,(to vary the axial overlap of the reinforcement tube 4 and the window portion 26),so that it is possible to cover the acoustic window portion 26 (see FIG. 3) or to expose it (see FIG. 4) by way of the reinforcement tube 4.

The following description will explain an operation of the ultra-sound catheter 1 disclosed here when observing the inside of a body lumen.

Before inserting the sheath 2 of the ultra-sound catheter 1 inside the body lumen, a priming operation is carried out for filling the inside of the ultra-sound catheter 1 with physiological saline solution. By carrying out this priming operation, it is possible to remove the air inside the ultra-sound catheter 1 and to inhibit or prevent air from entering inside of the body lumen of the blood vessel or the like.

With respect to the priming operation, first, the physiological salt solution is injected into the port 311 while the hub 31 is pulled to the maximum extent toward the hand-side of the user (i.e., in the proximal direction), that is in a state in which the inner tube 312 is pulled proximally from the outer tube 331 to the maximum extent. The injected physiological salt solution is to be filled sequentially from the hub 31 to the inside of the sheath 2. When the ultra-sound catheter 1 is filled perfectly or completely with the physiological salt solution, the physiological salt solution is removed from the priming lumen 221 which is formed in the sheath distal member 21 of the sheath 2. Thus, the filling of the physiological salt solution can be confirmed. It is also possible to confirm the filling (complete filling) of the physiological saline solution by the fact that the physiological saline solution is discharged from the priming lumen 221 and the physiological saline solution overflows from the port 311. Priming is also necessary between the reinforcement tube 4 and the sheath 2, and by immersing the reinforcement tube 4 into the physiological saline solution, it is possible to carry out the priming between the reinforcement tube 4 and the sheath 2 from a hole of the reinforcement tube 4. Alternatively, it is possible to employ a construction in which the priming liquid flows out between the reinforcement tube 4 and the sheath 2 from the outer tube hold portion 65 and in which by sealing between the outer surface of the reinforcement tube 4 and the inner surface of the outer tube hold portion 65 by way of a sealing member, it is possible to carry out the priming also between the reinforcement tube 4 and the sheath 2 from the port 311.

Next, as shown in FIG. 10, the ultra-sound catheter 1 is connected to the external drive apparatus 80. More specifically, the male connector 51 is connected to the female connector of the external drive apparatus 80, and the unit connector main body 61 is connected to the sheath support portion 822 of the external drive apparatus 80.

Figure 3:
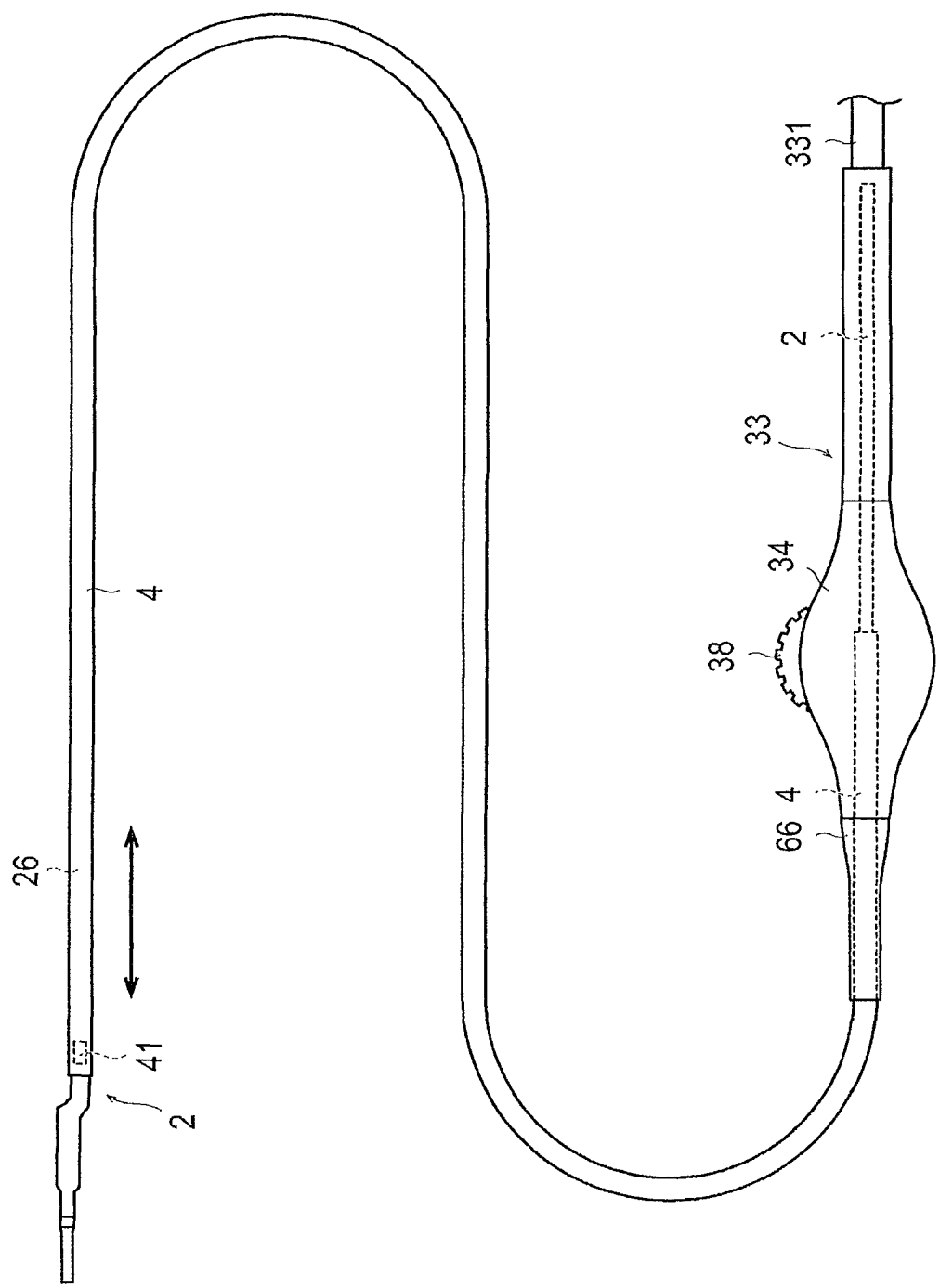
FIG. 3 is a plan view of the ultra-sound catheter when moving a reinforcement tube toward the distal side maximally.

Next, the hub 31 is axially moved in the distal direction to achieve a state in which the inner tube 312 is moved to the maximum distal extent inside the outer tube 331. Further, by manually rotating the operation dial 38, the reinforcement tube 4 is moved in the distal direction and the acoustic window portion 26 is covered by the reinforcement tube 4 as shown in FIG. 3 (i.e., the reinforcement tube 4 axially overlaps the window portion 26). In this state, the sheath 2 is inserted into the inside of the body. The insertion of the sheath 2 is stopped once the distal end portion of the sheath 2 is positioned adjacent the target lesion, e.g., exceeds or is moved distally beyond the target lesion.

The acoustic window portion 26 has a relatively low rigidity but is covered and reinforced by the reinforcement tube 4 so that the sheath 2 is relatively easily pushed without bending the window portion 26. If the acoustic window portion 26 was bent by pushing the sheath 2, the guide wire 25 (see FIGS. 14 and 15) would extend toward the direction spaced apart from the sheath and could, for example, touch a thin blood vessel and cause damage to the tissue. Because the acoustic window portion 26 is not so susceptible to such bending, safety is improved.

Next, the position of the sheath 2 is fixed and by manually rotating the operation dial 38, the reinforcement tube 4 is moved proximally toward the hand-side and the acoustic window portion 26 is exposed as illustrated in FIG. 4. Thereafter, as shown in FIG. 5 and FIG. 6, the transducer unit 41 is moved in the axial direction by proximally moving the hub 31, that is by pulling the hub 31 toward the hand-side or in the proximal direction. The region extending from a position forward of the target lesion to a position rearward of the target lesion is thus observed by the transducer unit 41 through the acoustic window portion 26. That is, a region including the target lesion, and portions distal and proximal of the target lesion, is observed by the transducer unit 41.

The ultra-sound catheter 1 according to this disclosed example of a first embodiment includes the acoustic window portion 26 having relatively high ultra-sound permeability, and also includes the reinforcement tube 4 which can cover the acoustic window portion 26, so that when inserting it inside the body lumen, the work performance thereof can be heightened by covering the acoustic window portion 26 having a relatively low rigidity by using the reinforcement tube 4, and on an occasion of observation, it is possible, by moving the reinforcement tube 4 to expose the acoustic window portion 26, to carry out the observation through the acoustic window portion 26 having high ultra-sound permeability.

Figure 11:
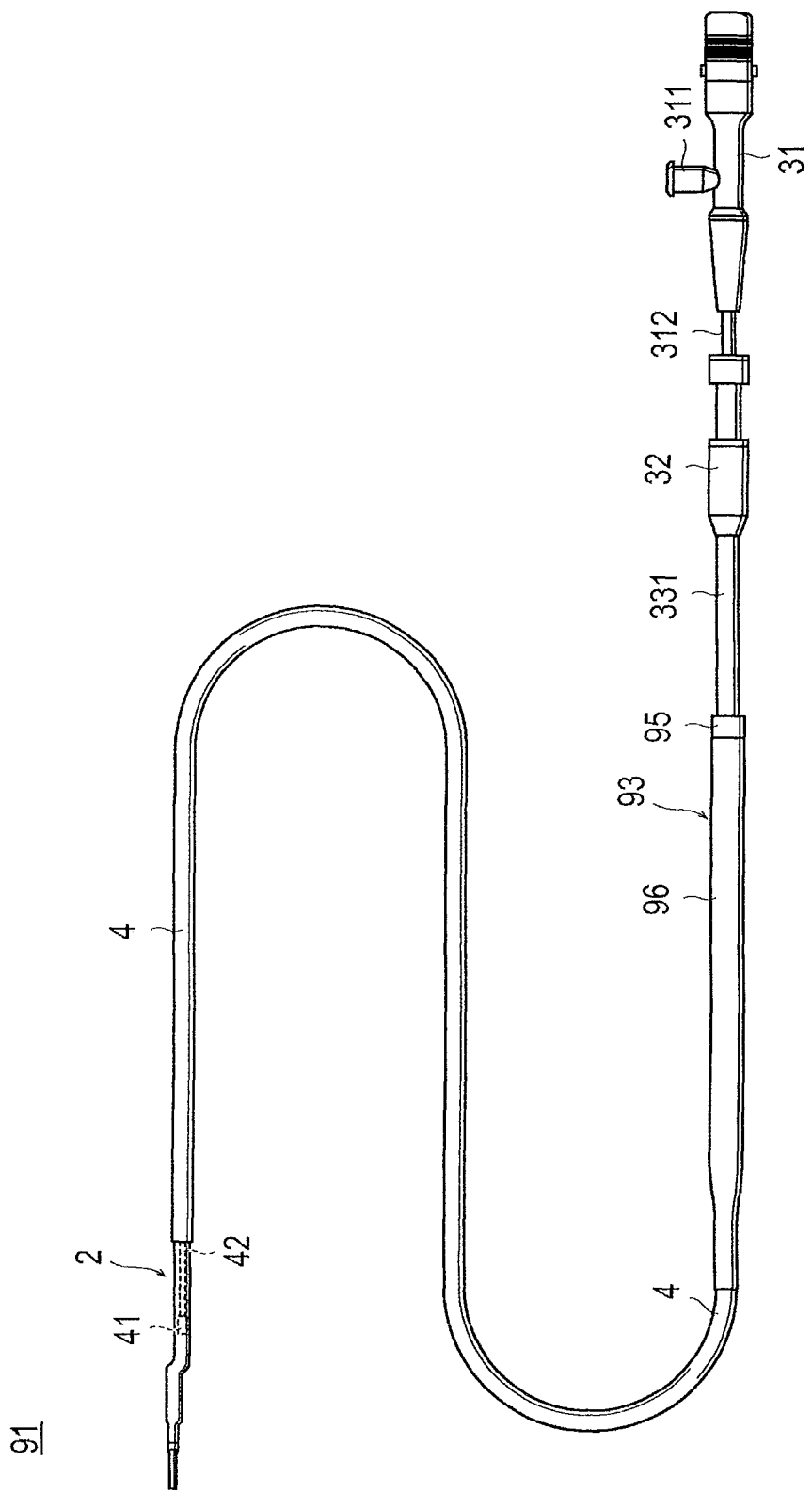
FIG. 11 is a plan view of an ultra-sound catheter according to a second embodiment disclosed by way of example.

The catheter described above as one example of a first embodiment is provided with a reinforcement tube steering unit 34 for steering movement of the reinforcement tube 4. FIG. 11 illustrates an example of a second embodiment of an ultra-sound catheter 91 which is not provided with a reinforcement tube steering unit. The description of the second embodiment which follows focuses primarily on differences between the second embodiment and the embodiment described above. Features of the second embodiment of the ultrasound catheter that are similar to those described above are identified by the same reference numerals, and a detailed description of such features is not repeated.

A relay connector 93 of the ultra-sound catheter 91 includes, as shown in FIG. 11, an outer tube hold portion 95 and a relay connector main body 96.

The outer tube hold portion 95 holds the outer tube 331. Also, the proximal end portion of the sheath 2 is connected to the inner surface of the outer tube hold portion 95, and there is formed a path for introducing the drive shaft 42 passing through from the outer tube 331 and the physiological salt solution into the sheath 2.

The relay connector main body 96 is an anti-kink protector which is longer than the relay connector main body 66 of the first embodiment and which is connected to the distal side of the outer tube hold portion 95, and it helps prevent the bending (kinking) of the reinforcement tube 4 and the sheath 2, which is caused by a rapid change of rigidity, while covering and protecting the outer surface of the reinforcement tube 4.

In the ultra-sound catheter 91 according to this second embodiment, it is possible, by directly steering or axially moving the reinforcement tube 4 which is exposed on the distal side away from the relay connector main body 96, to move the reinforcement tube 4 forward and backward, and to open and close (axially cover and uncover) the acoustic window portion 26.

The ultra-sound catheter 1 described above as an example of a first embodiment includes a reinforcement tube steering unit 34 for steering the movement of the reinforcement tube 4. This makes it possible to steer the reinforcement tube 4 forward and backward in the axial direction separately from the imaging core 40. But variations on this embodiment are possible. For example, as shown in FIG. 12, an ultra-sound catheter 101 according to a third embodiment is not provided with a reinforcement tube steering unit, and the reinforcement tube 4 is moved in synchronization with the imaging core 40 (transducer unit 41). The following description of the third embodiment focuses primarily on differences between the third embodiment and the embodiment described above. Features of the third embodiment of the ultrasound catheter similar to those described above in the first embodiment are identified by the same reference numerals, and a detailed description of such features is not repeated.

A relay connector 107 of the ultra-sound catheter 101 includes, as shown in FIG. 12, an outer tube hold portion 103 and a relay connector main body 102.

The outer tube hold portion 103 holds the outer tube 331. Also, the proximal end portion of the sheath 2 is connected to the inner surface of the outer tube hold portion 103, and there is formed a path for introducing the drive shaft 42 passing through from the outer tube 331 and the physiological salt solution into the sheath 2.

The relay connector main body 102 is an anti-kink protector which is longer than the relay connector main body 66 of the first embodiment and which is connected to the distal end portion of the outer tube hold portion 103, and it helps prevent the bending (kink) of the reinforcement tube 4 and the sheath 2, which is caused by a rapid change of rigidity, while covering protecting the outer surface of the reinforcement tube 4.

Figure 13:
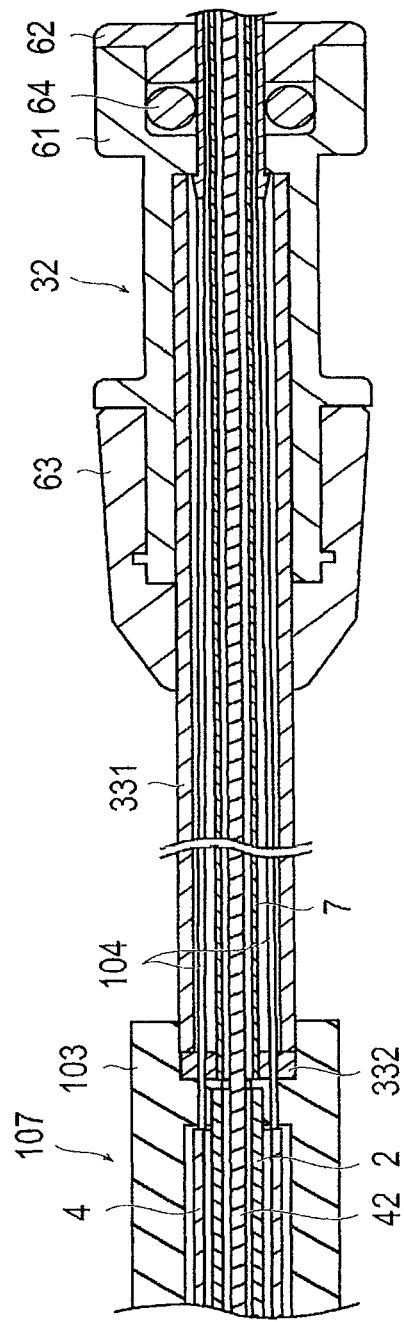
FIG. 13 is a longitudinal cross-sectional view of a unit connector and a relay connector when pulling an inner tube of the ultra-sound catheter according to the third embodiment maximally.

FIG. 13 shows a longitudinal cross-sectional view of the unit connector 32 and the relay connector 107 when proximally moving the inner tube 312, or pulling the inner tube 312, to the maximum extent. The distal end of the inner tube 312 and the proximal end of the reinforcement tube 4, which are positioned to sandwich the outer tube hold portion 103, are connected, as shown in FIG. 12 and FIG. 13, by a connecting rod 104 passing through a through-hole formed at the outer tube hold portion 103. In this embodiment, the connecting rod 104 is in the form of two pieces spaced apart in the circumferential direction, but the number of connecting rods can be other than two. The inner tube 312 moves forward and backward together with the imaging core 40 along with the movement of the hub 31 and therefore, the reinforcement tube 4 connected to the inner tube 312 will move forward and backward together with the imaging core 40.

The distal side of the reinforcement tube 4 is arranged on the proximal side away from the transducer unit 41 of the imaging core 40, but in a relatively close relationship with the transducer unit 41. Then, as the reinforcement tube 4 moves forward and backward together with the imaging core 40, the reinforcement tube 4 never covers the transducer unit 41.

Figure 14:
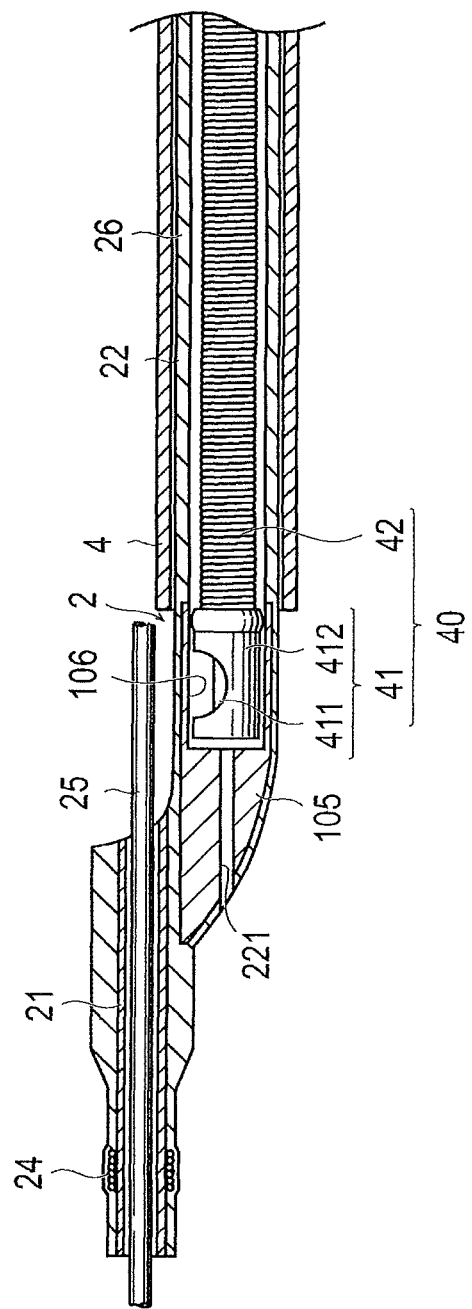
FIG. 14 is a longitudinal cross-sectional view of a junction portion between a distal portion and a main body unit of the ultra-sound catheter according to the third embodiment.

A filling-liquid in/out-path member 105 between the sheath distal member 21 and the sheath main body unit 22 as shown in FIG. 14 is in the form of a housing unit 106 (housing-unit), which can accommodate the transducer unit 41, in communication with the lumen in the inside of the sheath main body unit 22. The filling-liquid in/out-path member 105 is formed by a material whose rigidity is higher than that of the acoustic window portion 26.

In the embodiment of the ultrasound catheter shown in FIG. 2, the distal end of the reinforcement tube 4 is always positioned slightly on the proximal side of the transducer unit 41 so that the transducer unit 41 is not covered by the reinforcement tube 4. But this also means that the distal end portion of the acoustic window portion 26 is not reinforced by the reinforcement tube 4. The embodiment of the ultra-sound catheter shown in FIGS. 14 and 15 includes the filling-liquid in/out-path member 105 which is configured to receive the transducer unit 41 and reinforce the distal end portion of the acoustic window portion 26.

Set forth below is a description of the operation of the ultra-sound catheter 101 when observing the inside of a body lumen using the ultra-sound catheter 101 according to this third embodiment.

First, a priming operation is carried out for filling the inside of the ultra-sound catheter 101 with a physiological saline solution and the ultra-sound catheter 101 is connected to the external drive apparatus 80 as depicted in FIG. 10.

Next, the hub 31 is moved in the distal direction, and in a state in which the inner tube 312 is moved distally to the maximum extent in the outer tube 331 and also in a state in which the transducer unit 41 is housed in the housing unit 106 and the acoustic window portion 26 is covered by the reinforcement tube 4 as illustrated in FIG. 14, the sheath 2 is inserted inside the body and the insertion is stopped after the distal end of the sheath 2 exceeds the target lesion. At that time, the acoustic window portion 26 is covered by the reinforcement tube 4, so that pushability, anti-kinking properties, following-ability and the like are excellent, and it is possible to move the sheath until the aimed position is reached. Also, it is difficult for the acoustic window portion 26 to bend as discussed above and so safety is improved.

Figure 15:
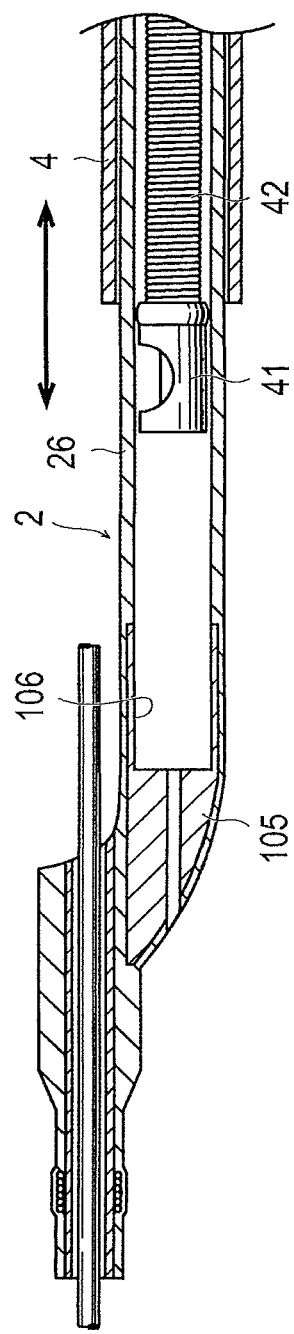
FIG. 15 is a longitudinal cross-sectional view showing the junction portion between the distal portion and the main body unit when moving an imaging core of the ultra-sound catheter in the third exemplified embodiment.

Next, while pulling the hub 31 in the proximal direction toward the hand-side as shown in FIG. 15, the transducer unit 41 is axially pulled out from the housing unit 106, and the region extending over the forward and backward portions of the target lesion is observed by the transducer unit 41 through the acoustic window portion 26. At that time, the transducer unit 41 axially moves forward and backward together with the reinforcement tube 4, so that while accomplishing reinforcement by a configuration in which the acoustic window portion 26 up to the proximal side of the transducer unit 41 is always covered by the reinforcement tube 4, it is possible to maintain the exposure of the acoustic window portion 26 in the region in which the transducer unit 41 is arranged. In addition, the reinforcement tube 4 can be steered simultaneously by steering the hub 31, so that relatively excellent steerability can be exerted even without providing the separate reinforcement tube steering unit 34 such as seen in the first embodiment.

The catheter here is not limited by the embodiments described above and illustrated in the accompanying drawing figures, as these are examples of the disclosed catheter, and it is possible to introduce various alterations. For example, the embodiments described above are discussed in the context of being used, by way of example, an ultra-sound catheter. But it is also possible to apply the disclosure to another catheter for diagnosis. For example, it is possible to apply the disclosure to a catheter for diagnosis utilizing optical coherence tomography (OCT). In OCT, it is possible to observe a living body by entering a measurement light into the living body and based on the light returning after being scattered or being absorbed, or after being reflected or being refracted inside the living body. Consequently, it is possible for the detection wave to apply not only the ultra-sound but also all kinds of detection waves which are applicable for the detection of such as light, magnetic field, sound and the like.

Also, the embodiments mentioned above used, for the detection unit, a transducer unit for carrying out both the transmission and the reception, but it is also possible to employ a relatively simple construction in which the detection wave illuminated inside the living body from a position different from that of the catheter is only received (detected) by the detection unit of the catheter.

The embodiments of the catheter described above include the reinforcement tube 4 covering the outside of the acoustic window portion 26. It is also possible though to employ a construction in which the inside of the acoustic window portion 26 is covered. Also, in order to move the reinforcement tube 4 in conjunction with the imaging core 40 such as shown in the third embodiment, it is also possible to employ a construction in which the reinforcement tube is interlinked with the driving power source of the external drive apparatus 80.

Also, the first embodiment employs a construction in which the operation dial 38 is rotated manually, but if a slide member provided on the case main body slidably is to be interlinked to the reinforcement tube 4, it is also possible to move the reinforcement member 4 by moving the slide member forward and backward without using the rotation force.

The detailed description above describes features and aspects of embodiments of a catheter. But the invention here is not limited to the precise embodiments and variations described. Changes, modifications and equivalents can be implemented without departing from the spirit and scope of the invention as defined in the accompanying claims. It is expressly intended that all such changes, modifications and equivalents which fall within the scope of the claims are embraced by the claims.

What is claimed is:

1. A catheter comprising:
   a sheath configured to be positioned in a body lumen of a living body, the sheath including a window portion permeable to inspection waves;
   a detection unit which receives inspection waves reflected from tissue of the body lumen and passing through the window portion of the sheath, the window portion possessing an axial extent extending from a distal-most end of the window portion to a proximal-most end of the window portion, the detection unit being axially movably positioned inside the sheath;
   a drive shaft connected to the detection unit so that axial movement of the drive shaft results in axial movement of the detection unit, the drive shaft being positioned inside the sheath;
   reinforcement positionable to axially overlap an entirety of the axial extent of the window portion of the sheath and reinforce a portion of the sheath that includes the entirety of the axial extent of window portion, at least a portion of the reinforcement being axially movable relative to the sheath so that the portion of the reinforcement is movable from a position in axial overlapping relation to the window portion of the sheath to a position in non-axial overlapping relation to the window portion of the sheath;
   a hub connected to the drive shaft so that axial movement of the hub results in axial movement of the drive shaft and the detection unit, the hub possessing a proximal-most end; and
   the reinforcement possessing a proximal-most end located distally of the proximal-most end of the hub.

2. The catheter according to claim 1, wherein the detection unit is a transducer unit which transmits ultrasound through the window portion of the sheath and receives reflected ultrasound through the window portion of the sheath.

3. The catheter according to claim 1, further comprising a rotatable operation dial operatively connected to the portion of the reinforcement so that operation of the operation dial axially moves the portion of the reinforcement.

4. The catheter according to claim 3, wherein the reinforcement includes a reinforcement tube constituting the portion of the reinforcement that is axially movable, and wherein the operation dial is mounted in a main body, the main body housing a pair of rotation members which are both in contact with an outer surface of the reinforcement tube, one of the rotation members being fixed to the operation dials so that operation of the operation dial results in rotation of the one rotation member.

5. The catheter according to claim 1, wherein the reinforcement includes a reinforcement tube constituting the portion of the reinforcement that is axially movable, and wherein the reinforcement tube and the detection unit are axially fixed relative to one another so that the reinforcement tube is not axially movable relative to the detection unit, and a distal-most end of the reinforcement tube is positioned proximally of a distal end of the detection unit so that the distal-most end of the detection unit is distal of the distal-most end of the reinforcement tube.

6. The catheter according to claim 1, wherein the sheath includes a sheath distal member provided with a through hole configured to receive a guide wire to guide movement of the catheter toward a target site in the body lumen.

7. A catheter comprising:
   a sheath configured to be positioned in a body lumen of a living body and provided with a window portion permeable to inspection waves, the window portion of the sheath possessing an inner surface and an outer surface, the window portion possessing an axial extent extending from a distal-most end of the window portion to a proximal-most end of the window portion;
   a detection unit which detects the inspection waves passing through the window portion of the sheath, the detection unit being positioned inside the sheath and being axially movable inside the sheath; and
   reinforcement being configured to cover an entirety of the axial extent of the window portion, at least a portion of the reinforcement being axially movable relative to the sheath so that the portion of the reinforcement is movable from a position in covering relation to the window portion of the sheath in which the portion of the reinforcement covers the inner or the outer surface of the window portion of the sheath, to a position in non-covering relation to the window portion in which the portion of the reinforcement covers neither the inner surface nor the outer surface of the window portion of the sheath.

8. The catheter according to claim 7, wherein the reinforcement includes a reinforcement tube constituting the portion of the reinforcement that is axially movable, and further comprising a reinforcement tube steering unit operatively connected to the reinforcement tube to axially move the reinforcement tube along an axial extent of the sheath.

9. The catheter according to claim 8, wherein the reinforcement tube steering unit includes a main body fixed to the sheath and a rotation member rotatably mounted on the main body, the rotation member being operatively linked with the reinforcement tube so that rotation of the rotatable member results in axial movement of the reinforcement tube.

10. The catheter according to claim 7, wherein the reinforcement includes a reinforcement tube constituting the portion of the reinforcement that is axially movable, and wherein the reinforcement tube and the detection unit are axially fixed relative to one another so that the reinforcement tube is not axially movable relative to the detection unit, and a distal-most end of the reinforcement tube is positioned proximally of a distal end of the detection unit so that the distal-most end of the detection unit is distal of the distal-most end of the reinforcement tube.

11. The catheter according to claim 7, further comprising:
a drive shaft positioned inside the sheath and fixed to the detection unit to transmit a mechanical driving force to the detection unit by way of the drive shaft;
a hub for axially moving the drive shaft in an axial direction of the sheath; and
wherein the portion of the reinforcement is interlinked to the hub and is axially movable together with the hub and the drive shaft.

12. The catheter according to claim 7, wherein a distal end portion of the sheath includes a housing unit configured to accommodate the detection unit.

13. The catheter according to claim 7, wherein the sheath includes a sheath distal member provided with a through hole configured to receive a guide wire to guide movement of the catheter toward a target site in the body lumen.

14. A method comprising:
inserting a catheter in a body lumen of a living body, the catheter comprising a sheath provided with a window portion permeable to inspection waves, and a detection unit axially movably positioned inside the sheath, the window portion possessing an axial extent extending from a distal-most end of the window portion to a proximal-most end of the window portion;
moving the catheter until a distal end portion of the catheter is positioned adjacent a target lesion in the body lumen, the moving of the catheter being performed while an entirety of the axial extent of the window portion of the sheath is reinforced by reinforcement that axially overlaps the entirety of the axial extent of the window portion of the sheath;
axially moving at least a part of the reinforcement in a proximal direction relative to the sheath to uncover at least a proximal portion of the window portion of the sheath;
directing inspection waves at the body lumen; and
receiving at the detection unit reflected inspection waves which have reflected off the body lumen and passed through the window portion of the sheath.

15. The method according to claim 14, wherein the sheath includes a sheath distal member provided with a through hole, and wherein the catheter is moved to a position adjacent the target lesion in the body lumen by moving the catheter along a guide wire passing though the through hole in the sheath distal member.

16. The method according to claim 14, wherein the axially moving of the part of the reinforcement in the proximal direction to uncover the proximal portion of the window portion of the sheath comprises rotating an operation dial to axially move the part of the reinforcement.

17. The method according to claim 14, wherein the axially moving of the part of the reinforcement in the proximal direction to uncover the proximal portion of the window portion of the sheath comprises rotating an operation dial connected to a rotation member which is in contact with an outer surface of the part of the reinforcement to rotate the rotation member and axially move the part of the reinforcement tube.

18. The catheter according to claim 1, wherein the reinforcement includes a reinforcement portion covering a distal portion of the window portion and accommodating the detection unit when the detection unit is positioned at a distal-most position, the reinforcement also including an axially movable reinforcement tube constituting the portion of the reinforcement that is axially movable, the reinforcement portion and the reinforcement tube each possessing a distal end, the distal end of the reinforcement portion being located distal of the distal end of the reinforcement tube.

19. The catheter according to claim 7, wherein the reinforcement includes a reinforcement portion covering a distal portion of the window portion and accommodating the detection unit when the detection unit is positioned at a distal-most position, the reinforcement also including an axially movable reinforcement tube constituting the portion of the reinforcement that is axially movable, the reinforcement portion and the reinforcement tube each possessing a distal end, the distal end of the reinforcement portion being located distal of the distal end of the reinforcement tube.

20. The method according to claim 14, wherein the axially moving of the part of the reinforcement in the proximal direction relative to the sheath includes axially moving a reinforcement tube in the proximal direction relative to the sheath, the reinforcement also comprising a reinforcement portion covering a distal portion of the window portion and accommodating the detection unit when the detection unit is positioned at a distal-most position.

* * * * *